(12) United States Patent
Essner

(10) Patent No.: US 9,156,898 B2
(45) Date of Patent: Oct. 13, 2015

(54) TREATMENT OF CANCER AND COMPOSITIONS

(75) Inventor: Richard Essner, Santa Monica, CA (US)

(73) Assignee: John Wayne Cancer Institute, Santa Monica, CA (US)

( * ) Notice: Subject to any disclaimer, the term of this patent is extended or adjusted under 35 U.S.C. 154(b) by 0 days.

(21) Appl. No.: 13/243,914

(22) Filed: Sep. 23, 2011

(65) Prior Publication Data
US 2012/0258056 A1 Oct. 11, 2012

Related U.S. Application Data

(63) Continuation of application No. 11/249,589, filed on Oct. 12, 2005, now abandoned.

(60) Provisional application No. 60/618,409, filed on Oct. 12, 2004.

(51) Int. Cl.
C07K 14/47 (2006.01)
C12Q 1/68 (2006.01)

(52) U.S. Cl.
CPC .......... C07K 14/4748 (2013.01); C12Q 1/6886 (2013.01); *C12Q 2600/106* (2013.01); *C12Q 2600/112* (2013.01); *C12Q 2600/118* (2013.01); *C12Q 2600/136* (2013.01); *C12Q 2600/158* (2013.01)

(58) Field of Classification Search
USPC ......... 435/6, 91.1, 91.31, 455, 458, 6.1, 6.13, 435/6.14; 514/1, 2, 44; 536/23.1, 24.3, 536/24.5; 424/59
See application file for complete search history.

(56) References Cited

U.S. PATENT DOCUMENTS

| 6,444,195 | B1 * | 9/2002 | Cole et al. ........................ 424/60 |
| 7,332,290 | B2 * | 2/2008 | Rubin et al. ................... 435/7.1 |
| 7,618,814 | B2 * | 11/2009 | Bentwich ................... 435/320.1 |
| 2007/0203333 | A1 * | 8/2007 | McSwiggen et al. ......... 536/24.5 |

FOREIGN PATENT DOCUMENTS

WO WO 03/006477 * 1/2003

OTHER PUBLICATIONS

Yoshioka et al., Proc. Nat'l. Acad. Sci. vol. 100, No. 12, pp. 7247-7252 (2003).*
Yang et al., Nature, vol. 393, pp. 809-812 (1998).*
Ohashi et al., J. Biol. Chem., vol. 274, No. 5, pp. 3577-3648 (2010).*
Khvorova et al., Coll, vol. 115, pp. 209-216 (2003).*

* cited by examiner

*Primary Examiner* — Jane Zara
(74) *Attorney, Agent, or Firm* — Koppel, Patrick, Heybl & Philpott; Michael J. Ram

(57) ABSTRACT

The invention discloses a method of identifying a gene associated with stage III primary cancer or lymph node metastasis. The genes so identified include CAV1, CST3, LIMK1, MMP2, MMP15, VEGF, ETV4, MMP9, PIK3C2B, and SERPIN1. Also disclosed are methods for diagnosis, prognosis, and treatment of cancer. The invention further discloses compositions for preventing and treating diseases.

3 Claims, 2 Drawing Sheets

|  |  | P - Values |  |
|---|---|---|---|
| Genes | Kruskal-Wallis | Linear Regression | Spearman's Rho |
| CAV1 | 0.013 | 0.038 | 0.013 |
| LIMK1 | 0.006 | 0.006 | 0.001 |
| MMP15 | 0.035 | 0.043 | 0.010 |
| VEGF | 0.013 | 0.025 | 0.011 |

Disease State 1 = Stage I/II Primary Melanoma (Group 1)
Disease State 2 = Stage III Primary Melanoma (Group 3)
Disease State 3 = Matching Lymph Node Metastasis (Group 4)

|  | P - Values | | |
|---|---|---|---|
| Genes | Kruskal-Wallis | Linear Regression | Spearman's Rho |
| CAV1 | 0.021 | 0.012 | 0.004 |
| LIMK1 | 0.005 | 0.002 | 0.001 |
| MMP15 | 0.056* | 0.190* | 0.035 |
| VEGF | 0.039 | 0.009 | 0.008 |

Disease State 1 = Stage I/II Primary
Disease State 2 = Stage III Primary with SN met < 2mm
Disease State 3 = Stage III Primary with SN met ≥ 2mm
Disease State 4 = Lymph Node Metastasis

SEQUENCE LISTING

<160> NUMBER OF SEQ ID NOS: 33

<210> SEQ ID NO 1
<211> LENGTH: 21
<212> TYPE: RNA
<213> ORGANISM: Artificial sequence
<220> FEATURE:
<223> OTHER INFORMATION: Synthetic oligoribonucleotide

<400> SEQUENCE: 1
ccgcuacugc cccccaaacu g                                              21

<210> SEQ ID NO 2
<211> LENGTH: 21
<212> TYPE: RNA
<213> ORGANISM: Artificial sequence
<220> FEATURE:
<223> OTHER INFORMATION: Synthetic oligoribonucleotide

<400> SEQUENCE: 2
cuggccggcc accugccacu g                                              21

<210> SEQ ID NO 3
<211> LENGTH: 21
<212> TYPE: RNA
<213> ORGANISM: Artificial sequence
<220> FEATURE:
<223> OTHER INFORMATION: Synthetic oligoribonucleotide

<400> SEQUENCE: 3
accgcuacug cccccaaac u                                               21

<210> SEQ ID NO 4
<211> LENGTH: 21
<212> TYPE: RNA
<213> ORGANISM: Artificial sequence
<220> FEATURE:
<223> OTHER INFORMATION: Synthetic oligoribonucleotide

<400> SEQUENCE: 4
cuggcuccca ccugccccac a                                              21

<210> SEQ ID NO 5
<211> LENGTH: 21
<212> TYPE: RNA
<213> ORGANISM: Artificial sequence
<220> FEATURE:
<223> OTHER INFORMATION: Synthetic oligoribonucleotide

<400> SEQUENCE: 5
ccgagaccuc aacucccaca a                                              21

<210> SEQ ID NO 6
<211> LENGTH: 21
<212> TYPE: RNA
<213> ORGANISM: Artificial sequence
<220> FEATURE:
<223> OTHER INFORMATION: Synthetic oligoribonucleotide

<400> SEQUENCE: 6
ggaccgcuac ugcccccaa a                                               21

<210> SEQ ID NO 7
<211> LENGTH: 21
<212> TYPE: RNA
<213> ORGANISM: Artificial sequence

```
<220> FEATURE:
<223> OTHER INFORMATION: Synthetic oligoribonucleotide

<400> SEQUENCE: 7
ccggcgcggc gagagcggac u                                              21

<210> SEQ ID NO 8
<211> LENGTH: 21
<212> TYPE: RNA
<213> ORGANISM: Artificial sequence
<220> FEATURE:
<223> OTHER INFORMATION: Synthetic oligoribonucleotide

<400> SEQUENCE: 8
gagaccucaa cucccacaac u                                              21

<210> SEQ ID NO 9
<211> LENGTH: 21
<212> TYPE: RNA
<213> ORGANISM: Artificial sequence
<220> FEATURE:
<223> OTHER INFORMATION: Synthetic oligoribonucleotide

<400> SEQUENCE: 9 cugcccccccg agcuucuucc c                                             21

<210> SEQ ID NO 10
<211> LENGTH: 21
<212> TYPE: RNA
<213> ORGANISM: Artificial sequence
<220> FEATURE:
<223> OTHER INFORMATION: Synthetic oligoribonucleotide

<400> SEQUENCE: 10
ugggugcucu gagcaaauca c                                              21

<210> SEQ ID NO 11
<211> LENGTH: 21
<212> TYPE: RNA
<213> ORGANISM: Artificial sequence
<220> FEATURE:
<223> OTHER INFORMATION: Synthetic oligoribonucleotide

<400> SEQUENCE: 11
gggcagcucu gcccggcaga a                                              21

<210> SEQ ID NO 12
<211> LENGTH: 21
<212> TYPE: RNA
<213> ORGANISM: Artificial sequence
<220> FEATURE:
<223> OTHER INFORMATION: Synthetic oligoribonucleotide

<400> SEQUENCE: 12
cagccgccug cuccagcuga c                                              21

<210> SEQ ID NO 13
<211> LENGTH: 21
<212> TYPE: RNA
<213> ORGANISM: Artificial sequence
<220> FEATURE:
<223> OTHER INFORMATION: Synthetic oligoribonucleotide

<400> SEQUENCE: 13
ccaugggugc ucugagcaaa u                                              21
```

```
<210> SEQ ID NO 14
<211> LENGTH: 21
<212> TYPE: RNA
<213> ORGANISM: Artificial sequence
<220> FEATURE:
<223> OTHER INFORMATION: Synthetic oligoribonucleotide

<400> SEQUENCE: 14
caugggugcu cugagcaaau c                                              21

<210> SEQ ID NO 15
<211> LENGTH: 21
<212> TYPE: RNA
<213> ORGANISM: Artificial sequence
<220> FEATURE:
<223> OTHER INFORMATION: Synthetic oligoribonucleotide

<400> SEQUENCE: 15
augggugcuc ugagcaaauc a                                              21

<210> SEQ ID NO 16
<211> LENGTH: 21
<212> TYPE: RNA
<213> ORGANISM: Artificial sequence
<220> FEATURE:
<223> OTHER INFORMATION: Synthetic oligoribonucleotide

<400> SEQUENCE: 16
acggcccacc gggcuguggc a                                              21

<210> SEQ ID NO 17
<211> LENGTH: 21
<212> TYPE: RNA
<213> ORGANISM: Artificial sequence
<220> FEATURE:
<223> OTHER INFORMATION: Synthetic oligoribonucleotide

<400> SEQUENCE: 17
guggcaccga gcacucacac a                                              21

<210> SEQ ID NO 18
<211> LENGTH: 21
<212> TYPE: RNA
<213> ORGANISM: Artificial sequence
<220> FEATURE:
<223> OTHER INFORMATION: Synthetic oligoribonucleotide

<400> SEQUENCE: 18
auggcacgcc cauccgaaau g                                              21

<210> SEQ ID NO 19
<211> LENGTH: 21
<212> TYPE: RNA
<213> ORGANISM: Artificial sequence
<220> FEATURE:
<223> OTHER INFORMATION: Synthetic oligoribonucleotide

<400> SEQUENCE: 19
uggcacgccc auccgaaaug u                                              21

<210> SEQ ID NO 20
<211> LENGTH: 21
<212> TYPE: RNA
<213> ORGANISM: Artificial sequence
<220> FEATURE:
<223> OTHER INFORMATION: Synthetic oligoribonucleotide
```

<400> SEQUENCE: 20
cugccucacg ugugggaccu u                                              21

<210> SEQ ID NO 21
<211> LENGTH: 21
<212> TYPE: RNA
<213> ORGANISM: Artificial sequence
<220> FEATURE:
<223> OTHER INFORMATION: Synthetic oligoribonucleotide

<400> SEQUENCE: 21
ucccugucgc accaguacua u                                              21

<210> SEQ ID NO 22
<211> LENGTH: 21
<212> TYPE: RNA
<213> ORGANISM: Artificial sequence
<220> FEATURE:
<223> OTHER INFORMATION: Synthetic oligoribonucleotide

<400> SEQUENCE: 22
cccugagcuc uccggcuuau a                                              21

<210> SEQ ID NO 23
<211> LENGTH: 21
<212> TYPE: RNA
<213> ORGANISM: Artificial sequence
<220> FEATURE:
<223> OTHER INFORMATION: Synthetic oligoribonucleotide

<400> SEQUENCE: 23
gccucacgug ugggaccuuu a                                              21

<210> SEQ ID NO 24
<211> LENGTH: 21
<212> TYPE: RNA
<213> ORGANISM: Artificial sequence
<220> FEATURE:
<223> OTHER INFORMATION: Synthetic oligoribonucleotide

<400> SEQUENCE: 24
gcgcagcuac ugccauccaa u                                              21

<210> SEQ ID NO 25
<211> LENGTH: 21
<212> TYPE: RNA
<213> ORGANISM: Artificial sequence
<220> FEATURE:
<223> OTHER INFORMATION: Synthetic oligoribonucleotide

<400> SEQUENCE: 25
cagcgcagcu acugccaucc a                                              21

<210> SEQ ID NO 26
<211> LENGTH: 21
<212> TYPE: RNA
<213> ORGANISM: Artificial sequence
<220> FEATURE:
<223> OTHER INFORMATION: Synthetic oligoribonucleotide

<400> SEQUENCE: 26
uuggagccuu gccuugcugc u                                              21

<210> SEQ ID NO 27

```
<211> LENGTH: 21
<212> TYPE: RNA
<213> ORGANISM: Artificial sequence
<220> FEATURE:
<223> OTHER INFORMATION: Synthetic oligoribonucleotide

<400> SEQUENCE: 27
caggcugcac ccauggcaga a                                              21

<210> SEQ ID NO 28
<211> LENGTH: 21
<212> TYPE: RNA
<213> ORGANISM: Artificial sequence
<220> FEATURE:
<223> OTHER INFORMATION: Synthetic oligoribonucleotide

<400> SEQUENCE: 28
gugggccuug cucagagcgg a                                              21

<210> SEQ ID NO 29
<211> LENGTH: 21
<212> TYPE: RNA
<213> ORGANISM: Artificial sequence
<220> FEATURE:
<223> OTHER INFORMATION: Synthetic oligoribonucleotide

<400> SEQUENCE: 29
aggcgaggca gcuugaguua a                                              21

<210> SEQ ID NO 30
<211> LENGTH: 21
<212> TYPE: RNA
<213> ORGANISM: Artificial sequence
<220> FEATURE:
<223> OTHER INFORMATION: Synthetic oligoribonucleotide

<400> SEQUENCE: 30
ggcgaggcag cuugaguuaa a                                              21

<210> SEQ ID NO 31
<211> LENGTH: 21
<212> TYPE: RNA
<213> ORGANISM: Artificial sequence
<220> FEATURE:
<223> OTHER INFORMATION: Synthetic oligoribonucleotide

<400> SEQUENCE: 31
uugcucagag cggagaaagc a                                              21

<210> SEQ ID NO 32
<211> LENGTH: 21
<212> TYPE: RNA
<213> ORGANISM: Artificial sequence
<220> FEATURE:
<223> OTHER INFORMATION: Synthetic oligoribonucleotide

<400> SEQUENCE: 32
ugcccacuga ggaguccaac a                                              21

<210> SEQ ID NO 33
<211> LENGTH: 21
<212> TYPE: RNA
<213> ORGANISM: Artificial sequence
<220> FEATURE:
<223> OTHER INFORMATION: Synthetic oligoribonucleotide
```

```
<400> SEQUENCE: 33
gcccacugag gaguccaaca u                                        21
```

TREATMENT OF CANCER AND COMPOSITIONS

RELATED APPLICATION

This application is a continuation of U.S. patent application Ser. No. 11/249,589 now abandoned, filed Oct. 12, 2005, which claims priority to U.S. Provisional Application No. 60/618,409 filed on Oct. 12, 2004, the contents of which are incorporated herein by reference.

FIELD OF THE INVENTION

The present invention relates generally to cancer diagnosis, prognosis, and treatment. In particular, the invention relates to detection of genetic markers indicative of cancer such as melanoma, breast cancer, colon cancer, lung cancer, and merkel cell carcinoma in biological samples. The invention also relates to compositions for preventing and treating diseases, e.g., by administering the compositions topically to a subject.

BACKGROUND OF THE INVENTION

Both incidence and mortality from melanoma continue to rise in the United States. In 1992, the projected annual incidence and mortality from melanoma were 32,000 and 6,700, respectively.[1] By 2004, these figures had increased to 55,100 and 7,910, respectively.[2] The lifetime risk of developing melanoma was only 1:1500 in 1935, but had reached 1:75 in 2000.[3] The mortality rate due to melanoma correlates with advancing stage, which is determined by thickness and ulceration of the primary lesion, presence of regional lymph node (LN) metastasis or distant metastasis.[4] There is no adequately proven treatment for metastatic melanoma. Localized cutaneous melanoma is often curable by surgery alone, yet once lymph node metastasis occurs (which marks the beginning of AJCC (American Joint Committee on Cancer) stage III disease), likelihood of systemic disease and mortality increase. Whereas the estimated 10-year survival-rate for stage II melanoma patients is approximately 55%, that of stage III melanoma patients is only about 35%.[5]

Regional LN status is the single most important prognostic factor in melanoma. Patients with regional LN metastasis (AJCC stage III disease) have worse prognosis than those without (AJCC stage I/II), even if they have the same Breslow thickness.[5] Among the AJCC stage IV patients, the patients with no history of intervening stage III disease (no history of regional lymph node metastasis) have significantly better prognosis than those with history of intervening stage III disease (history of regional lymph node metastasis).[6] These findings suggest that lymph node metastasis is not just a passive event dependent on time, but rather an active event based upon differential metastatic potential among different primary lesions. Furthermore, ability of melanoma to metastasize to regional lymph nodes is an independent measure of overall aggressive potential. Therefore, identification of factors associated with, if not causative of, regional lymph node metastasis is a crucial step in understanding pathophysiology of regional and possibly distant metastasis.

SUMMARY OF THE INVENTION

One object of the invention is to provide genetic markers and methods for diagnosis, prognosis, and treatment of cancer. Another object of the invention is to provide compositions for preventing and treating diseases.

More specifically, in one aspect, the invention features a method of identifying a gene associated with stage III primary cancer or lymph node metastasis. The method comprises identifying a metastasis-associated gene differentially expressed in stage I or II primary cancer than in stage III primary cancer, analyzing the expression of the gene in the stage I or II primary cancer and the stage III primary cancer or lymph node metastasis, and relating the expression of the gene to the stage III primary cancer, the lymph node metastasis, or a combination thereof.

In another aspect, the invention features a method of determining whether a subject is likely to be suffering from stage III cancer. The method comprises providing a test sample from a subject and detecting the expression of one or more genes selected from a first group consisting of CAV1 (caveolin 1), CST3 (cystatin C), LIMK1 (LIM domain kinase 1), MMP2 (matrix metallopeptidase 2), MMP15 (matrix metallopeptidase 15), VEGF (vascular endothelial growth factor), ETV4 (ETS variant gene 4), MMP9 (matrix metallopeptidase 9), PIK3C2B (phosphoinositide-3-kinase, class 2, beta polypeptide), and SERPIN1 (serpin peptidase inhibitor 1) in the sample. The expression of one or more genes selected from a second group consisting of CAV1, CST3, LIMK1, MMP2, MMP15, and VEGF in the sample, if higher than its respective control value, the expression of one or more genes selected from a third group consisting of ETV4, MMP9, PIK3C2B, and SERPIN1 in the sample, if lower than its respective control value, or a combination thereof, indicates that the subject is likely to be suffering from stage III cancer. In one embodiment, the control value is the expression level of the gene in a stage I or II primary tumor sample.

The invention also provides a method of staging cancer. The method comprises providing a test sample from a subject and detecting the expression of one or more genes selected from a first group consisting of CAV1, LIMK1, MMP15, and VEGF in the sample. The level of the expression of the one or more genes indicates that the subject is likely to be suffering from stage I or II primary cancer, stage III primary cancer with micrometastasis, stage III primary cancer with macrometastasis, or lymph node metastasis. In one embodiment, the one or more genes are selected from a second group consisting of CAV1, LIMK1, and VEGF, and the level of the expression of the one or more genes indicates that the subject is likely to be suffering from stage III primary cancer with micrometastasis or stage III primary cancer with macrometastasis. In another embodiment, the one or more genes are selected from a third group consisting of LIMK1 and VEGF.

The invention further provides a method of identifying a candidate compound for treating stage III cancer. The method comprises providing a stage III cancer cell that expresses one or more genes selected from a first group consisting of CAV1, CST3, LIMK1, MMP2, MMP15, VEGF, ETV4, MMP9, PIK3C2B, and SERPIN1, contacting the cell with a test compound, and detecting the expression of the one or more genes selected from the first group in the cell. The expression of one or more genes selected from a second group consisting of CAV1, CST3, LIMK1, MMP2, MMP15, and VEGF, if lower than its respective control value, the expression of one or more genes selected from a third group consisting of ETV4, MMP9, PIK3C2B, and SERPIN1, if higher than its respective control value, or a combination thereof, indicates that the test compound is a candidate for treating stage III cancer.

Another method of identifying a candidate compound for treating cancer comprises providing a system that expresses one or more genes selected from a first group consisting of CAV1, CST3, MMP15, ETV4, MMP9, PIK3C2B, and SERPIN1, contacting the system with a test compound, and detecting the expression of the one or more genes selected from the first group in the system. The expression of one or more genes selected from a second group consisting of CAV1, CST3, and MMP15, if lower than its respective control value, the expression of one or more genes selected from a third group consisting of ETV4, MMP9, PIK3C2B, and SERPIN1, if higher than its respective control value, or a combination thereof, indicates that the test compound is a candidate for treating cancer.

Also within the invention is a method of treating stage III cancer. The method comprises identifying a subject suffering from stage III cancer and administering to the subject one or more compounds that decrease the expression of one or more genes selected from a first group consisting of CAV1, CST3, LIMK1, MMP2, MMP15, and VEGF, increase the expression of one or more genes selected from a second group consisting of ETV4, MMP9, PIK3C2B, and SERPIN1, or a combination thereof, in the subject.

In yet another aspect, the invention features a method of treating cancer. The method comprises identifying a subject suffering from cancer as staged using the method described above and administering to the subject one or more compounds that decrease the expression of one or more genes selected from a first group consisting of CAV1, CST3, LIMK1, MMP2, MMP15, and VEGF, increase the expression of one or more genes selected from a second group consisting of ETV4, MMP9, PIK3C2B, and SERPIN1, or a combination thereof, in the subject.

Another method of treating cancer comprises identifying a subject suffering from cancer and administering to the subject one or more compounds selected from a group consisting of a first compound that inhibits the expression of CAV1, a second compound that inhibits the expression of CST3, a third compound that inhibits the expression of MMP15, a fourth compound that enhances the expression of ETV4, a fifth compound that enhances the expression of MMP9, a sixth compound that enhances the expression of PIK3C2B, and a seventh compound that enhances the expression of SERPIN1.

An alternative method of treating cancer comprises identifying a subject suffering from cancer and administering to the subject a combination of at least two (e.g., at least three, four, five, six, seven, eight, nine, and ten) compounds selected from the group consisting of a first compound that inhibits the expression of CAV1, a second compound that inhibits the expression of CST3, a third compound that inhibits the expression of LIMK1, a fourth compound that inhibits the expression of MMP2, a fifth compound that inhibits the expression of MMP15, a sixth compound that inhibits the expression of VEGF, a seventh compound that enhances the expression of ETV4, an eighth compound that enhances the expression of MMP9, a ninth compound that enhances the expression of PIK3C2B, and a tenth compound that enhances the expression of SERPIN1. The combination is not a first combination of the third and fourth compounds, a second combination of the third and sixth compounds, a third combination of the fourth and sixth compounds, or a fourth combination of the third, fourth, and sixth compounds.

The methods of the invention are applicable to different types of cancer, including and not limited to melanoma, breast cancer, colon cancer, lung cancer, or merkel cell carinoma. A test sample from a subject can be a freshly prepared tumor sample, a frozen tumor sample, a paraffin-embedded tumor sample, a primary tumor sample, a metastasis sample, or a blood sample. When a compound is administered to a subject, it may be administered topically. In some embodiments, the compound is administered with a transdermal drug delivery agent. For example, the compounds may be admixed with a lotion, cream (e.g., sunscreen cream), emulsion, oil, liquid, or gel, or embedded in a patch.

Further, the invention features a composition for preventing and treating diseases. The composition comprises one or more therapeutic compounds and a transdermal drug delivery agent such as a lotion, cream (e.g., sunscreen cream), emulsion, oil, liquid, gel, or patch. The one or more compounds may regulate the expression of one or more genes in a subject. In one embodiment, the one or more genes are associated with cancer such as melanoma, breast cancer, colon cancer, lung cancer, or merkel cell carinoma. Examples of such genes include, but are not limited to, CAV1, CST3, LIMK1, MMP2, MMP15, VEGF, ETV4, MMP9, PIK3C2B, and SERPIN1.

Another composition of the invention comprises a combination of at least two (e.g., at least three, four, five, six, seven, eight, nine, and ten) compounds selected from the group consisting of a first compound that inhibits the expression of CAV1, a second compound that inhibits the expression of CST3, a third compound that inhibits the expression of LIMK1, a fourth compound that inhibits the expression of MMP2, a fifth compound that inhibits the expression of MMP15, a sixth compound that inhibits the expression of VEGF, a seventh compound that enhances the expression of ETV4, an eighth compound that enhances the expression of MMP9, a ninth compound that enhances the expression of PIK3C2B, and a tenth compound that enhances the expression of SERPIN1. The combination is not a first combination of the third and fourth compounds, a second combination of the third and sixth compounds, a third combination of the fourth and sixth compounds, or a fourth combination of the third, fourth, and sixth compounds. The compounds may be admixed with or embedded in a transdermal drug delivery agent.

A compound of the invention can be an siRNA, ribozyme, antisense nucleotide, transcription factor decoy, or small molecule. In particular, a compound that decreases the expression of LIMK1 may be an siRNA targeting LIMK1 mRNA at CCGCUACUGCCCCCAAACUG, CUGGCCGGCCAC-CUGCCACUG, ACCGCUACUGCCCCCAAACU, CUG-GCUCCCACCUGCCCCACA, CCGAGACCUCAACUC-CCACAA, GGACCGCUACUGCCCCCAAA, CCGGCGCGGCGAGAGCGGACU, GAGACCU-CAACUCCCACAACU, CUGCCCCCCGAGCUUCU-UCCC, UGGGUGCUCUGAGCAAAUCAC, or GGGCAGCUCUGCCCGGCAGAA, or an siRNA targeting dLIMK1 mRNA at CAGCCGCCUGCUCCAGCUGAC, CCAUGGGUGCUCUGAGCAAAU, CAUGGGUGCU-CUGAGCAAAUC, AUGGGUGCUCUGAGCAAAUCA, ACGGCCCACCGGGCUGUGGCA, GUGGCACCGAG-CACUCACACA, AUGGCACGCCCAUCCGAAAUG, UGGCACGCCCAUCCGAAAUGU, CUGCCUCACGU-GUGGGACCUU, UCCCUGUCGCACCAGUACUAU, CCCUGAGCUCUCCGGCUUAUA, or GCCUCACGU-GUGGGACCUUUA. A compound that decreases the expression of VEGF may be an siRNA targeting VEGF mRNA at GCGCAGCUACUGCCAUCCAAU, CAGCGCAGC-UACUGCCAUCCA, UUGGAGCCUUGCCUUGCUGCU, CAGGCUGCACCCAUGGCAGAA, GUGGGCCUUGCU-CAGAGCGGA, AGGCGAGGCAGCUUGAGUUAA, GGCGAGGCAGCUUGAGUUAAA, UUGCUCAGAGCG-GAGAAAGCA, UGCCCACUGAGGAGUCCAACA, or GCCCACUGAGGAGUCCAACAU.

In addition, the invention provides a kit for detecting gene expression. The kit consists of a combination of at least two (e.g., at least three, four, five, six, seven, eight, nine, and ten) agents selected from the group consisting of a first agent for detecting the expression of CAV1, a second agent for detecting the expression of CST3, a third agent for detecting the expression of LIMK1, a fourth agent for detecting the expression of MMP2, a fifth agent for detecting the expression of MMP15, a sixth agent for detecting the expression of VEGF, a seventh agent for detecting the expression of ETV4, an eighth agent for detecting the expression of MMP9, a ninth agent for detecting the expression of PIK3C2B, and a tenth agent for detecting the expression of SERPIN1, wherein the combination is not a first combination of the third and fourth agents, a second combination of the third and sixth agents, a third combination of the fourth and sixth agents, or a fourth combination of the third, fourth, and sixth agents. The kit can be used in the diagnostic, prognostic, and drug screening methods of the invention.

As used herein, "one or more" refers to any and every combination of genes, compounds, etc. It encompasses a combination of at least two, three, four, five, six, seven, eight, nine, ten, and more genes, compounds, etc.

The above-mentioned and other features of this invention and the manner of obtaining and using them will become more apparent, and will be best understood, by reference to the following description, taken in conjunction with the accompanying drawings. These drawings depict only typical embodiments of the invention and do not therefore limit its scope.

DETAILED DESCRIPTION OF THE INVENTION

Figure 1:
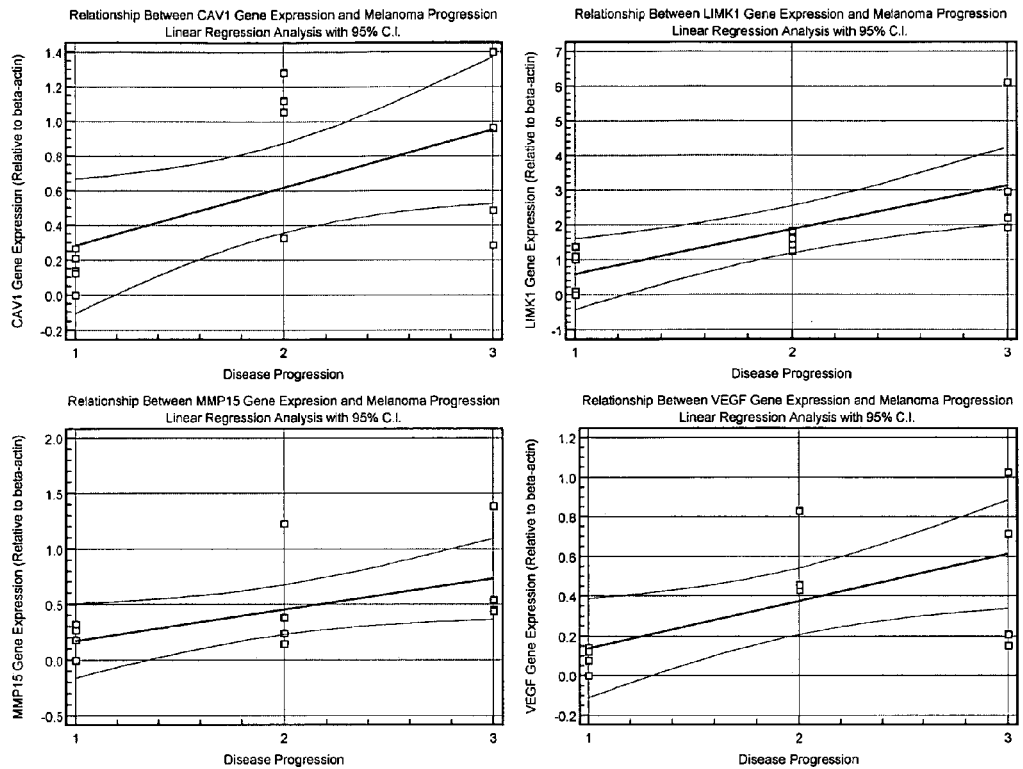
FIG. 1 depicts trend analysis of 10 genes noted to be differentially expressed between stage I/II and stage III primary melanoma. Regression lines and associated 95% confidence intervals are shown. CAV1, LIMK1, MMP15, and VEGF were noted to show a significant trend of increase as the melanoma progressed from stage I/II primary lesion to lymph node metastasis. Five primary melanomas from stage I/II, and 4 matching pairs of stage III primary melanoma and lymph node metastasis were used; 2 matching pairs were cell lines (CRL 7425 & 7426, and IGR 37 & 39) and 2 other matching pairs were from 2 different stage III patients (primary and sentinel lymph node metastasis).

The ability of a tumor to metastasize to regional LNs may require expression of particular sets of metastasis genes by a cluster of cells within the primary tumor, resulting in clonal heterogeneity and selective clonal metastasis.[7, 8] The genes that may aid in cellular extravasation, motility, neovascularization, and growth factors have all been implicated in process of tumor invasion, metastasis, and growth.[9-12] A recent in vitro study using allogeneic human melanoma cell lines shows that primary and metastatic melanoma express different sets of genes.[13] Another in vitro study shows that melanoma cell lines with different metastatic potential express different metastasis-associated genes.[14]

In the Examples described below, using fresh human tissue and functionally-focused cDNA microarray restricted to metastasis-associated genes, we have analyzed and identified unexpected differential expression of metastasis-associated genes between primary melanomas with and without LN metastasis (stage I/II vs. stage III). We further show that, surprisingly, some of these genes are progressively up-regulated in the LN metastases, suggesting true functional relevance of these genes in melanoma progression and metastasis.

Accordingly, it is an object of the present invention to provide a method of identifying a gene associated with stage III primary cancer or lymph node metastasis. The method comprises identifying a metastasis-associated gene differentially expressed in stage I or II primary cancer than in stage III primary cancer, analyzing the expression of the gene in the stage I or II primary cancer and the stage III primary cancer or lymph node metastasis, and relating the expression of the gene to the stage III primary cancer, the lymph node metastasis, or a combination thereof. Primary cancer is the first or original cancer. Metastasis refers to the migration of cancer cells from the original tumor site through the blood and lymph vessels to produce cancer in other tissues. The term is also used to refer to a secondary cancer growing at a distant site. Cancer stages are defined according to the AJCC Manual for Staging of Cancer. Generally, at stage I and II, the cancer is limited to the primary site. At stage III, the cancer spreads to the regional or adjacent lymph nodes. Rather than profiling via mass-gene arrays, focused analysis of gene-expression using functionally relevant gene microarrays can identify genes that are functionally significant.

Metastasis-associated genes are genes differentially expressed in non-metastatic or normal tissues than in metastatic tissues. They can be identified by comparing the expression levels of genes in non-metastatic or normal tissues and metastatic tissues. Many metastasis-associated genes are known in the art. To identify metastasis-associated genes differentially expressed in stage I or II primary cancer and stage III primary cancer, the expression levels of metastasis-associated genes in stage I or II primary cancer and stage III primary cancer can be determined and compared.

In general, gene expression can be detected and quantified at mRNA or protein level using a number of means well known in the art. To measure mRNA levels, cells in biological samples (e.g., cultured cells, tissues, and body fluids) can be lysed and the mRNA levels in the lysates or in RNA purified or semi-purified from the lysates determined by any of a variety of methods familiar to those in the art. Such methods include, without limitation, hybridization assays using detectably labeled gene-specific DNA or RNA probes and quantitative or semi-quantitative RT-PCR methodologies using appropriate gene-specific oligonucleotide primers. Alternatively, quantitative or semi-quantitative in situ hybridization assays can be carried out using, for example, unlysed tissues or cell suspensions, and detectably (e.g., fluorescently or enzyme-) labeled DNA or RNA probes. Additional methods for quantifying mRNA levels include RNA protection assay (RPA), cDNA and oligonucleotide microarrays, representation difference analysis (RDA), differential display, EST sequence analysis, and SAGE.

Methods of measuring protein levels in biological samples are also known in the art. Many such methods employ antibodies (e.g., monoclonal or polyclonal antibodies) that bind specifically to target proteins. In such assays, an antibody itself or a secondary antibody that binds to it can be detectably labeled. Alternatively, the antibody can be conjugated with biotin, and detectably labeled avidin (a polypeptide that binds to biotin) can be used to detect the presence of the biotinylated antibody. Combinations of these approaches (including "multi-layer sandwich" assays) familiar to those in the art can be used to enhance the sensitivity of the methodologies. Some of these protein-measuring assays (e.g., ELISA or Western blot) can be applied to bodily fluids or to lysates of test cells and others (e.g., immunohistological methods or fluorescence flow cytometry) applied to unlysed tissues or cell suspensions. Methods of measuring the amount of a label depend on the nature of the label and are known in the art. Appropriate labels include, without limitation, radionuclides (e.g., $^{125}$I, $^{131}$I, $^{35}$S, $^{3}$H, or $^{32}$P), enzymes (e.g., alkaline phosphatase, horseradish peroxidase, luciferase, or β-glactosidase), fluorescent moieties or proteins (e.g., fluorescein, rhodamine, phycoerythrin, GFP, or BFP), or luminescent moieties (e.g., Qdot™ nanoparticles supplied by the Quantum Dot Corporation, Palo Alto, Calif.). Other applicable assays include quantitative immunoprecipitation or complement fixation assays.

Once a metastasis-associated gene is found to be differentially expressed in stage I or II primary cancer than in stage III primary cancer, the expression of the gene in stage I or II primary cancer and stage III primary cancer or lymph node metastasis is analyzed. The expression of the gene is then related to stage III primary cancer, lymph node metastasis, or a combination thereof, using statistical methods well known in the art. Such statistical methods include, without limitation, Wilcoxon rank sum, Fisher's exact, Kruskal-Wallis, and Pearson goodness-of-fit tests, Spearman's (rho) rank correlation, Receiver-Operator Characteristic (ROC) curves, linear and ordinal regression models, and Sommers' D statistical significance determination. Genes identified as being related to stage III primary cancer, lymph node metastasis, or a combination thereof, are useful for diagnosis and prognosis of cancer, drug screening, and treatment of cancer as markers.

Generally, the diagnostic and prognostic methods involve identifying a subject suffering from cancer, providing a test sample from the subject, detecting gene expression in the sample, comparing the expression level to a control value, thereby determining the stage of the cancer or predicting the outcome of the cancer.

A "subject," as used herein, refers to human and non-human animals, including all vertebrates, e.g., mammals, such as non-human primates (particularly higher primates), sheep, dog, rodent (e.g., mouse or rat), guinea pig, goat, pig, cat, rabbits, cow, and non-mammals, such as chickens, amphibians, reptiles, etc. In a preferred embodiment, the subject is a human. In another embodiment, the subject is an experimental animal or animal suitable as a disease model. Identification of a candidate subject can be in the judgment of the subject or a health care professional, and can be subjective (e.g., opinion) or objective (e.g., measurable by a test or diagnostic method).

A test sample from a subject can be a tissue sample (e.g., a freshly prepared tumor sample, a frozen tumor tissue specimen, a paraffin-embedded tumor sample, a primary tumor sample, or a metastasis sample) or a body fluid sample (e.g., any body fluid in which cancer cells may be present, including, without limitation, blood, bone marrow, cerebral spinal fluid, peritoneal fluid, pleural fluid, lymph fluid, ascites, serous fluid, sputum, lacrimal fluid, stool, or urine). The tissues and body fluids can be collected using any of the methods well known in the art.

As described in the Examples below, six genes (CAV1, CST3, LIMK1, MMP2, MMP15, and VEGF; p<0.05) were significantly up-regulated in stage III primary melanoma. Four genes (ETV4, MMP9, PIK3C2B, and SERPIN1; p<0.05) were significantly down-regulated in stage III primary melanoma. Three genes (CAV1, LIMK1, and VEGF) were progressively up-regulated as the disease progressed. Trend analyses followed by ROC curve and multivariate ordinal regression analysis showed that LIMK1 (p=0.005) and VEGF (p=0.014) were independently predictive of melanoma progression and LN metastasis.

Accordingly, one diagnostic method of the invention involves providing a test sample from a subject, detecting the expression of CAV1, CST3, LIMK1, MMP2, MMP15, VEGF, ETV4, MMP9, PIK3C2B, or SERPIN1 in the sample, and comparing the gene expression level to its respective control value. If the expression of CAV1, CST3, LIMK1, MMP2, MMP15, or VEGF is higher than its respective control value, or the expression of ETV4, MMP9, PIK3C2B, or SERPIN1 is lower than its respective control value, the subject is likely to be suffering from stage III cancer. The control value is a predetermined expression level, e.g., an expression level relative to that of a reference gene (e.g., a housekeeping gene such as β-actin or GAPDH), or the expression level of a gene in a stage I or II primary tumor sample.

A second diagnostic method of the invention involves providing a test sample from a subject, detecting the expression of CAV1, LIMK1, MMP15, and VEGF in the sample, comparing the gene expression level to its respective control value, and determining whether the subject is likely to be suffering from stage I or II primary cancer, stage III primary cancer with micrometastasis (e.g., sentinel lymph node metastasis<2 mm), stage III primary cancer with macrometastasis (e.g., sentinel lymph node metastasis≥2 mm), or lymph node metastasis. The control value is a predetermined expression level, e.g., an expression level relative to that of a reference gene, the expression level of a gene in a control stage I or II primary cancer sample, the expression level of a gene in a control stage III primary cancer sample, the expression level of a gene in a control stage III primary cancer sample from a subject suffering from stage III primary cancer with micrometastasis, the expression level of a gene in a control stage III primary cancer sample from a subject suffering from stage III primary cancer with macrometastasis, or the expression level of a gene in a control lymph node metastasis sample.

A prognostic method of the invention involves providing a test sample from a subject suffering from cancer, detecting the expression of CAV1, CST3, LIMK1, MMP2, MMP15, VEGF, ETV4, MMP9, PIK3C2B, and SERPIN1 in the sample, comparing the gene expression level to its respective control value, and determining whether the cancer is likely to progress from stage I or II primary cancer to stage III primary cancer with micrometastasis, stage III primary cancer with macrometastasis, or lymph node metastasis.

This invention provides methods (also referred to as "screening assays") for identifying test compounds (e.g., siRNAs, ribozymes, antisense nucleotides, transcription factor decoys, small molecules, proteins, peptides, peptidomimetics, peptoids, antibodies, or other drugs) that regulate the expression of genes related to cancer. These compounds are useful for treating cancer.

The test compounds of the present invention can be obtained using any of the numerous approaches known in the art. siRNAs, ribozymes, antisense nucleotides, transcription factor decoys can be designed and synthesized using methods known in the art. See, e.g., Stevenson (2004) N Engl J Med 351: 1772-7; Mann and Conte (2003) Am J Cardiovasc Drugs 3(2): 79-85. Other test compounds may be obtained, for example, using combinatorial library methods known in the art. See, e.g., U.S. Pat. No. 6,462,187. Such libraries include, without limitation, peptide libraries, peptoid libraries (libraries of molecules having the functionalities of peptides, but with a novel, non-peptide backbone that is resistant to enzymatic degradation), spatially addressable parallel solid phase or solution phase libraries, synthetic libraries obtained by deconvolution or affinity chromatography selection, and the "one-bead one-compound" libraries. Compounds in the last three libraries can be peptides, non-peptide oligomers, or small molecules. Examples of methods for synthesizing molecular libraries can be found in the art. Libraries of compounds may be presented in solution, or on beads, chips, bacteria, spores, plasmids, or phages.

To identify a compound that regulates the expression of a gene, an in vitro transcription/translation mixture, a cell such as a cancer cell, or a subject expressing the gene is provided. The cell or subject may be a cell or subject that naturally expresses the gene, or alternatively, a cell or subject that expresses a recombinant form of the gene. Test compounds are added to the in vitro transcription/translation mixture or cell, or administered to the subject. The expression of the gene is determined and compared to a control value, e.g., an expression level relative to that of a reference gene, or the expression level of the gene prior to the addition or administration of a compound. If the expression level of the gene changes (increases or decreases), the compound is a candidate for treating cancer.

More specifically, one screening assay of the invention involves providing a stage III cancer cell (in culture or in a subject) that expresses CAV1, CST3, LIMK1, MMP2, MMP15, VEGF, ETV4, MMP9, PIK3C2B, or SERPIN1, contacting the cell with a test compound, and detecting the expression of the gene in the cell. If the expression of CAV1, CST3, LIMK1, MMP2, MMP15, or VEGF is lower than its respective control value, the expression of ETV4, MMP9, PIK3C2B, or SERPIN1 is higher than its respective control value, or a combination thereof, the test compound is a candidate for treating stage III cancer.

A second screening assay of the invention involves providing a system (an in vitro transcription/translation mixture, a cell, or a subject) that expresses CAV1, CST3, MMP15, ETV4, MMP9, PIK3C2B, or SERPIN1, contacting the system with a test compound, and detecting the expression of the gene in the system. If the expression of CAV1, CST3, or MMP15 is lower than its respective control value, the expression of ETV4, MMP9, PIK3C2B, or SERPIN1 is higher than its respective control value, or a combination thereof, the test compound is a candidate for treating cancer.

All the basic essential materials and reagents required for detecting gene expression can be assembled together in a kit. The kit may generally comprise agents (e.g., pre-selected primers or probes) specific for a panel of marker genes. Also included may be enzymes suitable for amplifying nucleic acids including various polymerases (reverse transcriptase, Taq, etc.), deoxynucleotides and buffers to provide the necessary reaction mixture for amplification. Such kit may further comprise, in suitable means, distinct containers for each individual reagent and enzyme as well as for each marker primer pair or probe. Kits of the present invention may include a means for containing the reagents in close confinement for commercial sale such as, e.g., injection or blow-molded plastic containers into which the desired reagent are retained. Other containers suitable for conducting certain steps of the disclosed methods also may be provided.

One kit that can be used in the diagnostic, prognostic, and drug screening methods of the invention consists of a combination of at least two agents selected from the group consisting of a first agent for detecting the expression of CAV1, a second agent for detecting the expression of CST3, a third agent for detecting the expression of LIMK1, a fourth agent for detecting the expression of MMP2, a fifth agent for detecting the expression of MMP15, a sixth agent for detecting the expression of VEGF, a seventh agent for detecting the expression of ETV4, an eighth agent for detecting the expression of MMP9, a ninth agent for detecting the expression of PIK3C2B, and a tenth agent for detecting the expression of SERPIN1. The combination is not a first combination of the third and fourth agents, a second combination of the third and sixth agents, a third combination of the fourth and sixth agents, or a fourth combination of the third, fourth, and sixth agents.

This invention additionally provides methods for treating cancer. The term "treating" is defined as administration of a substance to a subject with the purpose to cure, alleviate, relieve, remedy, prevent, or ameliorate a disorder, symptoms of the disorder, a disease state secondary to the disorder, or predisposition toward the disorder.

Identification of a candidate subject can be in the judgment of the subject or a health care professional, and can be subjective (e.g., opinion) or objective (e.g., measurable by a test or diagnostic method). For example, a subject to be treated can be identified by determining gene expression in a test sample prepared from the subject. If the expression of a gene is different (higher or lower) from a control value, the patient is a candidate for treatment with an effective amount of a compound that regulates (decreases or increases) the expression of the gene. An "effective amount" is an amount of the compound that is capable of producing a medically desirable result in a treated subject. The medically desirable result may be objective (i.e., measurable by some test or marker, e.g., decreased or increased expression of the gene) or subjective (i.e., subject gives an indication of or feels an effect). The treatment methods can be performed alone or in conjunction with other drugs and/or radiotherapy. See, e.g., U.S. Patent Application 20040224363.

In one in vivo approach, a therapeutic compound (e.g., a compound that regulates the expression of a gene or a compound identified as described above) itself is administered to the subject. As used herein, a "therapeutic compound" can mean a compound the administration of which results in complete abolishment of the symptoms of a disease, a decrease in the severity of the symptoms of the disease, or prevention of the symptoms of a disease. Generally, the compound will be suspended in a pharmaceutically-acceptable carrier and administered orally, or by intravenous (i.v.) infusion, or injected or implanted subcutaneously, intramuscularly, intrathecally, intraperitoneally, intrarectally, intravaginally, intranasally, intragastrically, intratracheally, or intrapulmonarily. Pharmaceutically acceptable carriers are biologically compatible vehicles that are suitable for administration to a subject, e.g., physiological saline or liposomes. For treatment of cancer, the compound is preferably delivered directly to tumor cells, e.g., to a tumor or a tumor bed following surgical excision of the tumor, in order to kill any remaining tumor cells. For prevention of cancer invasion and metastases, the compound can be administered to, for example, a subject that has not yet developed detectable invasion and metastases but whose primary tumor was found to express the gene. The dosage required depends on the choice of the route of administration, the nature of the formulation, the nature of the subject's illness, the subject's size, weight, surface area, age, and sex, other drugs being administered, and the judgment of the attending physician. Suitable dosages are in the range of 0.01-100.0 mg/kg. Wide variations in the needed dosage are to be expected in view of the variety of compounds available and the different efficiencies of various routes of administration. For example, oral administration would be expected to require higher dosages than administration by i.v. injection. Variations in these dosage levels can be adjusted using standard empirical routines for optimization as is well understood in the art. Encapsulation of the compound in a suitable delivery vehicle (e.g., polymeric microparticles or implantable devices) may increase the efficiency of delivery, particularly for oral delivery.

Topical administration of a therapeutic compound is useful when the desired treatment involves areas or organs readily accessible by topical application. For application topically to the skin, the compound can be formulated with a suitable ointment containing the compound suspended or dissolved in a carrier. Carriers for topical administration of the compound include, but are not limited to, mineral oil, liquid petroleum, white petroleum, propylene glycol, polyoxyethylene or polyoxypropylene compound, emulsifying wax, and water. Alternatively, the compound can be formulated with a suitable lotion or cream containing the compound suspended or dissolved in a carrier with suitable emulsifying agents. Suitable carriers include, but are not limited to, mineral oil, sorbitan monostearate, polysorbate 60, cetyl esters wax, cetearyl alcohol, 2-octyldodecanol, benzyl alcohol, and water. The therapeutic compound may also be topically applied to the lower intestinal tract by rectal suppository formulation or in a suitable enema formulation. A therapeutic compound can be delivered using transdermal technologies involving chemical enhancers, iontophoresis, adhesives, microneedles, gels, and sonophoresis. See, e.g., Chiarello, Pharmaceutical Technology, Oct. 2, 2004: 46-56.

In some embodiments, polynucleotides such as siRNAs, ribozymes, antisense nucleotides, and transcription factor decoys are administered to a subject. Polynucleotides can be delivered to target cells by, for example, the use of polymeric, biodegradable microparticle or microcapsule devices known in the art. Another way to achieve uptake of the nucleic acid is using liposomes, prepared by standard methods. The polynucleotides can be incorporated alone into these delivery vehicles or co-incorporated with tissue-specific or tumor-specific antibodies. Alternatively, one can prepare a molecular conjugate composed of a polynucleotide attached to poly-L-lysine by electrostatic or covalent forces. Poly-L-lysine binds to a ligand that can bind to a receptor on target cells. "Naked DNA" (i.e., without a delivery vehicle) can also be delivered to an intramuscular, intradermal, or subcutaneous site. A preferred dosage for administration of polynucleotide is from approximately $10^6$ to $10^{12}$ copies of the polynucleotide molecule.

Double-stranded interfering RNA (RNAi; including siRNA) homologous to a target gene can also be used to reduce the expression of the target gene. See, e.g., Stevenson (2004) N Engl Med 351: 1772-7. The sense and antisense RNA strands can be individually constructed using chemical synthesis and enzymatic ligation reactions using procedures known in the art. For example, each strand can be chemically synthesized using naturally occurring nucleotides or variously modified nucleotides designed to increase the biological stability of the molecule or to increase the physical stability of the duplex formed between the sense and antisense strands, e.g., phosphorothioate derivatives and acridine substituted nucleotides. The sense or antisense strand can also be produced biologically using an expression vector into which a target gene sequence (full-length or a fragment) has been subcloned in a sense or antisense orientation. The sense and antisense RNA strands can be annealed in vitro before delivery of the dsRNA to target cells. Alternatively, annealing can occur in vivo after the sense and antisense strands are sequentially delivered to the cancer cells. Double-stranded RNA interference can also be achieved by introducing into target cells a polynucleotide from which sense and antisense RNAs can be transcribed under the direction of separate promoters, or a single RNA molecule containing both sense and antisense sequences can be transcribed under the direction of a single promoter.

A polynucleotide containing a nucleic acid sequence that is transcribed into an antisense RNA complementary to the mRNA of a target gene (the full-length mRNA sequence or a suitable portion thereof) can be delivered to target cells. The polynucleotide can include one or more sequences complementary to the sense strand of a target gene and a catalytic sequence known to be responsible for mRNA cleavage. For example, a derivative of a Tetrahymena L-19 IVS RNA can be constructed in which the nucleotide sequence of the active site is complementary to the nucleotide sequence to be cleaved in a target mRNA. Alternatively, a target mRNA can be used to select a catalytic RNA having a specific ribonuclease activity from a pool of RNA molecules.

In the relevant polynucleotides (e.g., expression vectors), the nucleic acid sequence encoding the antisense RNA is operatively linked to a promoter or enhancer-promoter combination. Enhancers provide expression specificity in terms of time, location, and level. Unlike a promoter, an enhancer can function when located at variable distances from the transcription initiation site, provided a promoter is present. An enhancer can also be located downstream of the transcription initiation site. Suitable expression vectors include plasmids and viral vectors such as herpes viruses, retroviruses, vaccinia viruses, attenuated vaccinia viruses, canary pox viruses, adenoviruses and adeno-associated viruses, among others.

Transcription factor decoys are double-stranded nucleic acid molecules with high binding affinity for targeted transcription factors. See, e.g., Mann and Conte (2003) Am J Cardiovasc Drugs 3(2): 79-85; U.S. Pat. No. 6,821,956. Transcription factors are endogenous, sequence-specific double-stranded DNA binding proteins which modulate (increase or decrease) the rate of transcription of one or more specific genes in a cell. Methods for identifying transcription factor binding sequences are known in the art.

The length, structure, and nucleotide sequence of a decoy varies depending on the target transcription factor, the indication, route of administration, etc. In addition to binding affinity, decoys are also selected for binding specificity. A decoy contains sufficient nucleotide sequence to ensure target transcription factor binding specificity and affinity sufficient for therapeutic effectiveness. Typically, a transcription factor requires at least six base pairs, usually at least about eight base pairs for sufficient binding specificity and affinity. Frequently, providing a decoy with flanking sequences (ranging from about 5 to 50 bp) beside the binding site enhances binding affinity and/or specificity. The strands may be synthesized in accordance with conventional ways using phosphoramidite synthesis, commercially available automatic synthesizes, and the like.

One treatment method of the invention involves identifying a subject suffering from stage III cancer and administering to the subject therapeutic compounds to decrease the expression of CAV1, CST3, LIMK1, MMP2, MMP15, or VEGF, to increase the expression of ETV4, MMP9, PIK3C2B, or SERPIN1, or a combination thereof, in the subject.

Another treatment method of the invention involves identifying a subject suffering from cancer as staged using the method described above and administering to the subject therapeutic compounds to decrease the expression of CAV1, CST3, LIMK1, MMP2, MMP15, or VEGF, to increase the expression of ETV4, MMP9, PIK3C2B, or SERPIN1, or a combination thereof, in the subject.

A third treatment method of the invention involves identifying a subject suffering from cancer and administering to the subject a first compound that inhibits the expression of CAV1, a second compound that inhibits the expression of CST3, a third compound that inhibits the expression of MMP15, a fourth compound that enhances the expression of ETV4, a fifth compound that enhances the expression of MMP9, a sixth compound that enhances the expression of PIK3C2B, a seventh compound that enhances the expression of SERPIN1, or a combination thereof.

A fourth treatment method of the invention involves identifying a subject suffering from cancer and administering to the subject a combination of at least two compounds selected from the group consisting of a first compound that inhibits the expression of CAV1, a second compound that inhibits the expression of CST3, a third compound that inhibits the expression of LIMK1, a fourth compound that inhibits the expression of MMP2, a fifth compound that inhibits the expression of MMP15, a sixth compound that inhibits the expression of VEGF, a seventh compound that enhances the expression of ETV4, an eighth compound that enhances the expression of MMP9, a ninth compound that enhances the expression of PIK3C2B, and a tenth compound that enhances the expression of SERPIN1. The combination is not a first combination of the third and fourth compounds, a second combination of the third and sixth compounds, a third combination of the fourth and sixth compounds, or a fourth combination of the third, fourth, and sixth compounds.

In particular, a therapeutic compound that decreases the expression of LIMK1 may be an siRNA targeting LIMK1 mRNA at position 1869: CCGCUACUGCCCCCCAAACUG, at position 1996: CUGGCCGGCCACCUGCCACUG, at position 1868: ACCGCUACUGCCCCCCAAACU, at position 629: CUGGCUCCCACCUGCCCCACA, at position 1539: CCGAGACCUCAACUCCCACAA, at position 1866: GGACCGCUACUGCCCCCCAAA, at position 2061: CCGGCGCGGCGAGAGCGGACU, at position 1541: GAGACCUCAACUCCCACAACU, at position 1887: CUGCCCCCCGAGCUUCUUCCC, at position 420: UGGGUGCUCUGAGCAAAUCAC, at position 1017: GGGCAGCUCUGCCCGGCAGAA, or an siRNA targeting the splice variant of LIMK1 mRNA (dLIMK) at position 903: CAGCCGCCUGCUCCAGCUGAC, at position 417: CCAUGGGUGCUCUGAGCAAAU, at position 418: CAUGGGUGCUCUGAGCAAAUC, at position 419: AUGGGUGCUCUGAGCAAAUCA, at position 722: ACGGCCCACCGGGCUGUGGCA, at position 737: GUGGCACCGAGCACUCACACA, at position 845: AUGGCACGCCCAUCCGAAAUG, at position 846: UGGCACGCCCAUCCGAAAUGU, at position 495: CUGCCUCACGUGUGGGACCUU, at position 337: UCCCUGUCGCACCAGUACUAU, at position 980: CCCUGAGCUCUCCGGCUUAUA, or at position 497: GCCUCACGUGUGGGACCUUUA.

A therapeutic compound that decreases the expression of VEGF may be an siRNA targeting VEGF mRNA at position 1182: GCGCAGCUACUGCCAUCCAAU, at position 1180: CAGCGCAGCUACUGCCAUCCA, at position 1065: UUGGAGCCUUGCCUUGCUGCU, at position 1111: CAGGCUGCACCCAUGGCAGAA, at position 1538: GUGGGCCUUGCUCAGAGCGGA, at position 1628: AGGCAGGCAGCUUGAGUUAA, at position 1629: GGCGAGGCAGCUUGAGUUAAA, at position 1545: UUGCUCAGAGCGGAGAAAGCA, at position 1322: UGCCCACUGAGGAGUCCAACA, or at position 1323: GCCCACUGAGGAGUCCAACAU.

Furthermore, the invention provides compositions for preventing and treating diseases. In one embodiment, the composition comprises one or more therapeutic compounds and a transdermal drug delivery agent. A transdermal drug delivery agent refers to a substance that can be used to facilitate administration of a drug to a subject. Examples of such agent include, and are not limited to, a lotion, cream (e.g., sunscreen cream to protect a subject from the UV light), emulsion, oil, liquid, gel, or patch. The compounds may regulate the expression of one or more genes in a subject. For instance, the genes may be associated with cancer such as melanoma, breast cancer, colon cancer, lung cancer, or merkel cell carinoma. Examples of such genes include, without limitation, CAV1, CST3, LIMK1, MMP2, MMP15, VEGF, ETV4, MMP9, PIK3C2B, and SERPIN1.

The compounds of the invention can be incorporated into pharmaceutical compositions. Such compositions typically include the compounds and pharmaceutically acceptable carriers. A pharmaceutical composition is formulated to be compatible with its intended route of administration. See, e.g., U.S. Pat. No. 6,756,196. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol, or other synthetic solvents, antibacterial agents such as benzyl alcohol or methyl parabens, antioxidants such as ascorbic acid or sodium bisulfite, chelating agents such as ethylenediaminetetraacetic acid, buffers such as acetates, citrates, or phosphates, and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions that are suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.), or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it is preferable to include isotonic agents, for example, sugars, polyalcohols such as manitol, sorbitol, and sodium chloride in the composition. Prolonged absorption of the injectable compositions can be brought about by including in the composition an agent which delays absorption, for example, aluminum monostearate and gelatin.

Sterile injectable solutions can be prepared by incorporating the compounds in the required amounts in an appropriate solvent with one or a combination of ingredients enumerated above, as required, followed by filtered sterilization. Generally, dispersions are prepared by incorporating the compounds into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. For the purpose of oral therapeutic administration, the compounds can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin, an excipient such as starch or lactose, a disintegrating agent such as alginic acid, Primogel, or corn starch, a lubricant such as magnesium stearate or Sterotes, a glidant such as colloidal silicon dioxide, a sweetening agent such as sucrose or saccharin, or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the compounds are formulated into ointments, salves, gels, or creams as generally known in the art and described above.

The compounds can also be prepared in the form of suppositories (e.g., with conventional suppository bases such as cocoa butter and other glycerides) or retention enemas for rectal delivery.

In one embodiment, the compounds are prepared with carriers that will protect the compounds against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is advantageous to formulate oral or parenteral compositions in dosage unit form for ease of administration and uniformity of dosage. "Dosage unit form," as used herein, refers to physically discrete units suited as unitary dosages for the subject to be treated, each unit containing a predetermined quantity of active compound calculated to produce the desired therapeutic effect in association with the required pharmaceutical carrier.

Pharmaceutical compositions can be included in a container, pack, or dispenser together with instructions for administration to form packaged products. For example, a packaged product may comprise a container, an effective amount of a compound of the invention, and an insert associated with the container, indicating administering the compound for treating cancer.

A particular composition of the invention comprises a combination of at least two therapeutic compounds selected from the group consisting of a first compound that inhibits the expression of CAV1, a second compound that inhibits the expression of CST3, a third compound that inhibits the expression of LIMK1, a fourth compound that inhibits the expression of MMP2, a fifth compound that inhibits the expression of MMP15, a sixth compound that inhibits the expression of VEGF, a seventh compound that enhances the expression of ETV4, an eighth compound that enhances the expression of MMP9, a ninth compound that enhances the expression of PIK3C2B, and a tenth compound that enhances the expression of SERPIN1. The combination is not a first combination of the third and fourth compounds, a second combination of the third and sixth compounds, a third combination of the fourth and sixth compounds, or a fourth combination of the third, fourth, and sixth compounds. The compounds may be admixed with or embedded in a transdermal drug delivery agent.

The following examples are intended to illustrate, but not to limit, the scope of the invention. While such examples are typical of those that might be used, other procedures known to those skilled in the art may alternatively be utilized. Indeed, those of ordinary skill in the art can readily envision and produce further embodiments, based on the teachings herein, without undue experimentation.

EXAMPLES

Material and Methods
Experimental Design

This study utilized primary melanomas and/or sentinel LN(SLN) metastases from 12 AJCC clinical stage I/II (no palpable LN metastasis) melanoma patients and 2 matching pairs of cell lines derived from primary melanoma and LN metastasis from 2 different patients. The samples were divided into 4 groups as shown in Table 1. The study was divided into 2 stages. The first stage compared gene-expression differences between Group 1 and Group 2 by using a 96-gene cDNA microarray that is functionally-focused to metastasis-associated genes. After the differentially regulated genes were identified, as a partially validative procedure, the second stage analyzed the trend in expression levels of these genes as melanoma progressed from stage I/II primary melanoma (Group 1), to stage III primary melanoma (Group 3), to LN metastasis (Group 4).

TABLE 1

| Group 1 | Primary melanomas from stage I/II patients - No SLN metastasis (n = 5) |
|---|---|
| Group 2 | Primary melanomas from stage III patients - SLN metastasis (n = 5) |
| Group 3 | Primary melanomas from stage III patients with available matching SLN metastasis (n = 2) |
| | Cell lines derived from stage III primary melanomas (n = 2) |

TABLE 1-continued

| Group 4 | Matching SLN metastases from Group 3 patients (n = 2) Cell lines derived from matching LN metastases from Group 3 cell lines (n = 2) |

The samples are divided into 4 separate groups. The samples from Groups 3 & 4 are from 4 different patients (matching pairs of primary melanoma and LN metastasis).

Patient Population and Tissue Collection

Twelve consecutive AJCC clinical stage I/II patients (clinically negative LNs) with intact primary melanoma were accepted into the study at the John Wayne Cancer Institute under an IRB-approved protocol. Each patient had been diagnosed previously by an incisional biopsy of the primary melanoma. After informed consents were obtained, all patients underwent wide excision (WE) of their primary melanoma followed by lymphatic mapping and sentinel lymphadenectomy (SL), as previously described.[15, 16] In brief, the procedure was performed with pre-operative injection of $^{99m}$Tc-labeled sulfur-colloid lymphoscintigraphy to identify the nodal basin at risk for metastasis, followed by intraoperative peritumoral intradermal injection of isosulfan blue dye (Lymphazurin™, Tyco International, Norwalk, Conn.). The SLN was localized by using a hand-held gamma probe and by visual inspection for the presence of blue dye, which was used as the gold standard for identifying the SLNs.[17] The SLNs were evaluated for presence of metastasis by using routine H&E and immunohistochemical staining against S-100, HMB-45, and MART-1.

Tissue Processing and RNA Extraction

Portions of the primary melanoma and the sentinel lymph node were collected and placed immediately in RNAlater (Qiagen, Valencia, Calif.) for RNA preservation. Grossly melanotic portions were macro-dissected to contain>80% melanoma for primary melanomas, and approximately 100% melanoma for sentinel lymph node macrometastases (≥2 mm). RNA from each tissue specimen was extracted and purified by using RNeasy Kit (Qiagen, Valencia, Calif.) according to the manufacturer's instructions (RNeasy Mini Handbook). The initial RNA concentration and quality were assessed by optical densitometry at 260 nm and 280 nm. The final concentration, quality, and purity of total RNA were determined by using the RNA 6000 Nano Assay Kit on the Agilent 2100 Bioanalyzer (Agilent Technologies, Palo Alto, Calif.) per manufacturer's instructions (Agilent Bioanalyzer Handbook).

Cell Cultures

Four melanoma cell lines from two different stage III melanoma patients were commercially obtained (2 matching pairs of primary melanoma and LN metastasis). CRL-7425 and CRL-7426 (ATCC, Manassas, Va.) were derived from the primary melanoma and its lymph node metastasis in the same patient, respectively. Likewise, IGR-37 and IGR-39 (DSMZ, Braunschweig, Germany) were derived from a primary melanoma and its lymph node metastasis, respectively. CRL-7425 and CRL-7426 cell lines were grown in ATCC medium (90% DMEM with 4 mM L-glutamine adjusted to contain 1.5 g/L sodium bicarbonate and 4.5 g/L glucose, and 10% fetal bovine serum) and antibiotics at 37° C. in 5% $CO_2$ and 30% $O_2$. IGR-37 and IGR-39 cell lines were grown in 85% DMEM and 15% FBS with antibiotics at 37° C. in 5% $CO_2$ and 30% $O_2$. RNA was extracted as described in previous section.

Functionally-Focused cDNA Microarray

GEArray Q series—Human Tumor Metastasis Gene Array Kits (SuperArray, Bethesda, Md.)—were used per manufacturer's instructions with minor modifications (Modified protocol per courtesy of Dr. Y. Liu, JWCI). Each Q series array evaluates expression of 96 functionally-focused genes; the 112 gene-spots include 10 positive controls, 3 blanks, and 3 negative controls. Each gene-spot is sub-spotted 4 times to assure uniform hybridization. This cDNA microarray platform along with LPR amplification protocol has been cross-validated with RT-PCR by the manufacturer. Typically, 1 μg of extracted and purified RNA was reverse-transcribed into cDNA and then amplified into biotinylated (Biotin-16-dUTP) cDNA by LPR amplification protocol, per manufacturer's instructions. The biotinylated cDNA was placed on a microarray membrane that had been pre-hybridized with heat-denatured salmon sperm DNA, and hybridized overnight at 60° C. in a Lab-Line Instruments Hybridization Incubator 300 Series (Barnstead International, Dubuque, Iowa) while being continuously agitated at 10 rpm. Next day, the hybridization was blocked with blocking buffer, and arrays were washed with the washing buffer, both supplied by the manufacturer. Signal detection was performed by placing 200 μl of ECF chemiluminescent substrate (Amersham Pharmacia Biotech, UK, LTD.) on the array membrane and incubating it for 5 minutes in the dark at room temperature. The images were acquired on the Molecular Dynamics Storm 860 imaging station (Amersham Biosciences, Piscatanay, N.J.). The signal intensity, which corresponds to the amount of cDNA bound to the array, was analyzed by using ScanAlyze v.2.50 image analysis software (Lawrence Berkeley National Lab). Gene-expression levels were normalized to β-actin, which was chosen due to highly consistent and uniform inter-sample expression levels.

Statistical Analysis

Clinicopathologic differences between Group 1 (stage I/II, n=5) and Group 2 (stage III, n=5) patients were examined by using Fisher's exact test and Wilcoxon rank sum test. Univariate analysis for differential gene expression between Group 1 and Group 2 primary melanomas was done by using Wilcoxon rank sum test. Gene expression trend analysis used Spearman's (rho) rank correlation, Kruskal-Wallis test, and a linear regression model. Univariate analysis of classification accuracy for individual genes was done by using ROC curve analysis.[18, 19] Multivariate predictive analysis was done by building an ordinal regression model via stepwise selection of covariates, and model fit was evaluated with Pearson goodness-of-fit test and Sommers' D statistical significance was determined at p=0.05.

Results

Of 12 patients enrolled in the study, 5 had no SLN metastasis (AJCC stage I/II) and 7 had SLN metastasis (AJCC stage III). Among the 7 patients with SLN metastasis, 2 patients had RNA from primary melanoma and matching macroscopic (>2 mm) SLN metastasis available for in vivo matched-pair comparison; these 2 patients were excluded from the first stage of study (initial comparison of clinicopathologic features of Group 1 and Group 2 patients, and gene expression levels of their primary melanomas) so that they can be used later for a partially validative trend analysis in the second stage. Clinicopathologic features of the 2 groups are shown in Table 2. As expected, the two groups differed significantly by Breslow thickness of the primary and status of the SLNs, but not by other factors (age, gender, and ulceration). Gene-expression levels of these two groups were compared. Of the 96 functionally-focused metastasis-associated genes evaluated, 6 were significantly up-regulated (CAV1, CST3, LIMK1, MMP2, MMP15, and VEGF; p<0.05), and 4 were significantly down-regulated in stage III primary melanoma (ETV4, MMP9, PIK3C2B, and SERPIN1; p<0.05).

TABLE 2

Comparison of two groups used in initial univariate analysis

| | | Group 1 | Group 2 | P-value |
|---|---|---|---|---|
| n = | | 5 | 5 | |
| Age (yr) | | 70 ± 8.3 | 70 ± 18.3 | 0.54* |
| Gender | M | 5 | 3 | 0.44** |
| | F | 0 | 2 | |
| Breslow (mm) | | 1.71 ± 1.14 | 4.48 ± 2.55 | 0.01* |
| Ulceration | Present | 3 | 2 | >0.50** |
| | Absent | 1 | 3 | |
| | Unknown | 1 | 0 | |
| SN Metastasis Size (mm) | | 0 | 4.2 ± 5.15 | <0.001* |

*Wilcoxon Rank Sum Test
**Fisher's Exact Test
Two groups differed in Breslow thickness and presence of sentinel lymph node metastasis. They were not significantly different in other potential prognostic factors such as age, gender, and ulceration.

Association, however, does not equate to causation. Therefore we performed partially-validative trend analysis by using 5 original stage I/II primary melanomas (Group 1), 2 stage III primary melanomas from initially excluded stage III patients and 2 primary melanoma cell lines (CRL-7425 and IGR 37) (Group 3), and their matching lymph node metastases (2 matching SLN metastases, and matching LN metastasis cell lines CRL-7426, and IGR-39) (Group 4). The rationales for combining fresh tissue and cell lines are as follows. Genes identified by using in vivo tissue may be truly relevant in real life, but in vivo tissue suffers from tissue impurity. On the other hand, in vitro cell lines are clonally pure, but genes identified from them may represent in vitro artifact from the culture medium and conditions. However, if a gene is up-regulated (or down-regulated) in both in vivo tissue and in vitro cell lines, then its expression level most likely represents what happens real life, as it unlikely due to in vivo tissue impurity/contamination or in vitro artifact. In addition, the genes noted to be significant would have further in vitro testability.

Figure 2:
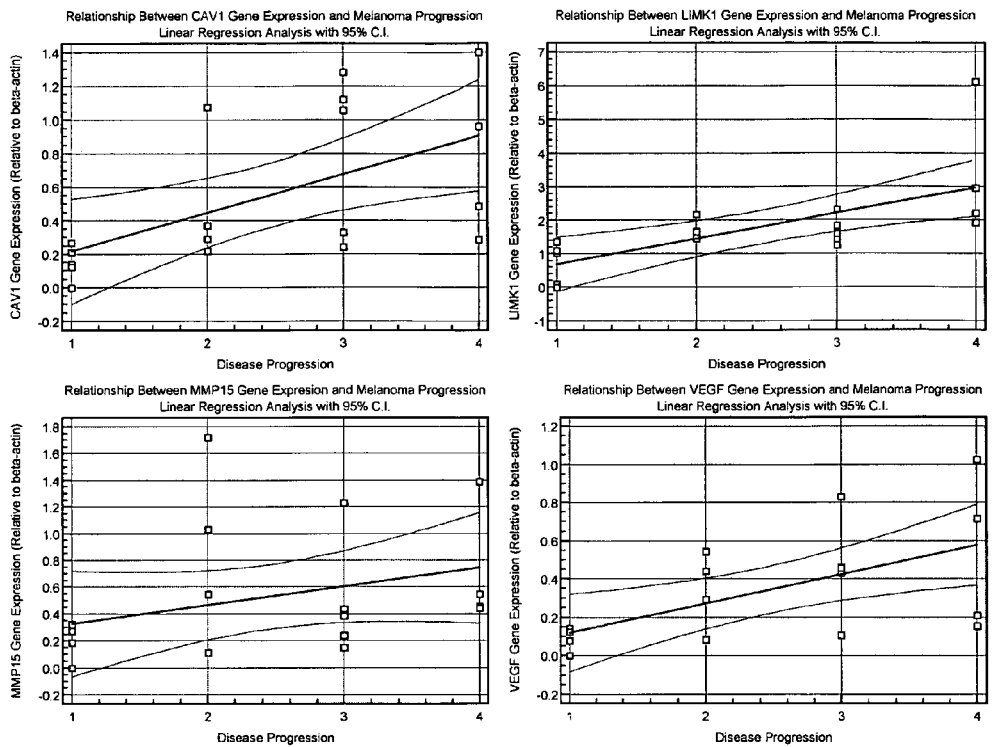
FIG. 2 shows the results of a test verifying whether the genes identified in trend analysis retain the same trend when additional prognostic category was added. Stage III patients were divided into 2 sub-prognostic groups (sentinel lymph node metastasis<2 mm vs.≥2 mm). Regression lines and associated 95% confidence intervals are shown. Whereas CAV1, LIMK1, and VEGF maintained significance, MMP15 failed to retain a significant trend.

Among the 10 genes identified to be differentially regulated between the Groups 1 and 2, 4 genes (CAV1, LIMK1, MMP15, and VEGF) showed consistent up-regulatory trend to be considered progressively up-regulated as the disease progressed from stage I/II primary melanoma (Group 1), to stage III primary melanoma (Group 3), to LN metastasis (Group 4) (FIG. 1). If these genes are truly involved in disease progression and metastasis, then they should be differentially expressed between the sub-prognostic categories of primary melanomas within the group of patients with stage III disease. Therefore, stage III primary melanomas were subcategorized by the size of their corresponding SLN metastasis (<2 mm vs.≥2 mm). Prognostic significance of micrometastasis vs. macrometastasis within the SLN has already been shown.[4, 5, 41] Similar trend analyses show that 3 out of 4 genes (CAV1, LIMK1, and VEGF) were progressively up-regulated as the disease progressed (FIG. 2). These data suggest that over-expression of CAV1, LIMK1, and VEGF genes are not only associated with higher likelihood of regional lymph node metastasis, but their degree of gene-expression correlate with differential metastatic potential.

Significant correlation, however, does not guarantee predictive or prognostic ability. If gene-expression levels show a high degree of variation among the individuals, and overlap between the groups within the population, then they may not have adequate predictive/prognostic power. To assess the potentials of these genes to correctly identify the primary melanomas with or without SLN metastasis, Receiver-Operator Characteristic (ROC) curves were constructed for the 3 identified genes. The areas under the curve (AUC) for CAV1, LIMK1, and VEGF were 0.943, 1.00, and 0.886, respectively. To compare, the documented AUCs for screening mammogram and MRI for high risk breast cancer patients are 0.686 and 0.827, respectively.[26] To identify the genes that can independently classify or predict the melanoma progression (stage I/II primary melanoma vs. stage III primary melanoma with micrometastasis vs. stage III primary melanoma with macrometastasis vs. LN metastasis), a multivariate ordinal regression analysis was performed. The covariates included in the model were CAV1, LIMK1, and VEGF. A stepwise selection of the covariates was used. This revealed that LIMK1 (P=0.005) and VEGF (P=0.014) are independently significant predictors of disease state, with combined concordance rate of 94.2% and good model fit [Pearson goodness-of-fit=0.83; Sommers' D (a measure of dependence and association)=0.88].

Discussion

The presence and extent of regional lymph node metastasis can have a significant impact on both management and prognosis of melanoma patients. Prognostic implications of tumor burden within the regional lymph nodes and within the sentinel lymph node have been already described by multiple investigators.[4, 5, 20-22] Management strategies based on SLN tumor burden are currently being studied under a National Cancer Institute sponsored multicenter international trial centered at the John Wayne Cancer Institute (MSLT-II). Recent attempts at outcome prediction by using Breslow thickness, ulceration, and sentinel lymph node tumor burden have provided enhanced risk stratification, yet power of prediction for a given individual remains inadequate.[20-22, 41] Perhaps then a better outcome prediction can be obtained by examining molecular factors. Advancement in utilization of immunohistochemical markers (i.e., ER/PR/Her2neu for breast cancer) now offers better risk stratification. Diagnostic and prognostic utility of multimarker RT-PCR for melanoma are currently being studied under prospective multi-institutional trials such as the Sunbelt Melanoma Trial and the Florida Melanoma Trial.[23-25] Biologically relevant molecular factors with adequate predictive power to determine disease states and/or outcomes are not only useful as biomarkers, but can also serve as potential targets for gene-mediated therapies.

Recent advancement in mass-screening methods, such as genomics and proteomics, now allow individual molecular profiling of the disease states or outcomes. However, the results obtained from these techniques are rarely duplicated or validated in repeated experiments. There are many potential reasons for this, and the problems exist beyond that of cross-platform validation. Several potential pitfalls must be addressed when designing experiments that rely on association and/or correlation. These include reliability of the sample integrity, validity of the comparisons made, biological relevance of identified genes/targets, and confounding covariates. Uniform sample collection and preparation protocols that minimize the amount and variation in sample degradation are required to maintain acceptable accuracy, as identical samples with differing amount of degradation will lead to different expression profiles. In our experience, expression of a reference gene, such as GAPDH, does not adequately infer integrity of RNA; we have found that GAPDH mRNA expression can be detected in the presence of severe RNA degradation detected by the Agilent Bioanalyzer. For this reason we used only uniformly collected fresh tissue preserved immediately in RNAlater in the operating room, and each sample was assessed for integrity and purity by using the Agilent Bioanalyzer.

Earlier cDNA microarray studies utilized universal reference mRNA, cell lines, or pooled tumor samples as the reference standard for comparison and determination of up- or down-regulation.[27-30] Although these strategies enable formulation of gene-expression profiles that can be correlated to a disease state or an outcome, the individual genes identified as up- or down-regulated cannot be considered biologically significant since their differential expressions were based on biologically irrelevant reference samples. Other investigators utilized surrounding "normal tissue" as the reference for comparison,[9, 10, 31, 32] however surrounding tissue contains more than just the cells that initiated tumor formation. The surrounding tissue lacks cellular homogeneity. In case of melanoma, ideal reference cells would be matching melanocytes, but for obvious reasons, this would be extremely difficult. For this reason, we compared stage I/II and stage III primary melanomas for our initial analysis. Our macro-dissection of the collected sample grossly yielded>80% melanoma (a very conservative estimate) for primary melanomas and near 100% melanoma for macroscopic sentinel lymph node metastases. Our control experiments showed that melanoma contains average of 5-fold greater amount of RNA than matching surrounding skin. By a calculated estimate, maximum amount of skin RNA contamination per μg of sample RNA would then be 4% (20% of 20%). To ensure that 4% skin RNA contamination did not influence our results, we compared gene-expression profiles of macro-dissected primary melanoma samples and matching surrounding skin located approximately 2 cm from the primary site. Results show that RNA from the surrounding skin samples contained several highly expressed genes that are not expressed in RNA from matching macro-dissected primary melanomas, suggesting that our melanoma samples did not contain appreciable amount of RNA contamination from the surrounding skin.

Our initial comparison of 5 stage I/II (Group 1) and 5 stage III (Group 2) primary melanomas showed that 10 genes were differentially regulated. To evaluate likelihood of their functional significance, their expression levels were examined in 3 progressive disease states (FIG. 1). The comparison shows that CAV1, LIMK1, MMP15, and VEGF were progressively up-regulated as melanoma progressed from stage I/II primary melanoma, to stage III primary melanoma, and to LN metastasis. Our trend analyses including 2 sub-prognostic groups within the stage III patients show that CAV1, LIMK1, and VEGF are progressively up-regulated as melanoma progressed from stage I/II primary melanoma to lymph node metastasis (FIG. 2). The ROC curve analyses show that expression levels of these genes can classify the stage of primary melanoma with high degree of accuracy (stage I/II vs. stage III: AUCs=0.943, 1.00, and 0.886 for CAV1, LIMK1, and VEGF, respectively). Multivariate ordinal regression analysis identified LIMK1 (p=0.005) and VEGF (p=0.014) as independent predictor of melanoma progression (Disease states 1-4 shown in FIG. 2) with 94.2% concordance rate and good model fit (Pearson goodness-of-fit=0.83; Sommers' D=0.88).

The significance of VEGF in tumor progression and metastasis has been shown in various tumor models, including melanoma.[11, 33, 34] Recent in vivo human study by Stefanou et al. showed that VEGF expression (by immunohistochemistry) was noted only in melanomas, but not in compound or dysplastic nevi. [34] Another in vitro human study by Simonetti et al. showed that none of the nevi, but 25% of in situ melanomas and 77% of primary invasive melanomas showed expression of VEGF detected by immunohistochemistry.[33] Their study also showed that MMP2 expression was higher in invasive melanomas when compared to in situ melanomas. This difference was not observed with MMP9. Our data from the initial comparison of Groups 1 and 2 are in agreement with these reported studies. Progressively higher VEGF mRNA expression was noted as melanoma progressed from stage I/II primary melanoma to lymph node metastasis (FIGS. 1 and 2). Although stage III primary melanomas expressed higher MMP2 and lower MMP9 mRNA than stage I/II primary melanomas, no significant trends were noted when we measured MMP2 and MMP9 gene expressions in the lymph node metastases. This does not mean that MMP2 is not important in melanoma invasion and metastasis, but rather, in our study MMP2 did not meet our strict screening and selection criteria for trend and significance.

Our data also show the importance of LIMK1, an important factor in actin cytoskeleton regulation and cellular cytokinesis, in melanoma progression and metastasis. LIMK1 is activated by ROCK (Rho associated serine-threonine protein kinase) and can inhibit cofilin activity by phosphorylation. [35-39] Cofilin plays a crucial role in actin depolymerization, and to date, is the only known target of LIMK1.[39] In vitro experiments using breast and prostate cancer cell lines, as well as in vivo animal experiments show mechanistic importance of LIMK1 over-expression in cancer invasion.[39] Since melanocytes have neuroectodermal embryonic origin, it is important to note that LIMK1 is highly expressed in neural tissue, and mice lacking LIMK1 gene show synaptic dysfunction.[39, 40] Although high expression of LIMK1 in melanoma has been previously reported,[39] to our knowledge, we are the first to report the importance of LIMK1 in melanoma progression and lymph node metastasis.

Presence of lymph node metastasis remains one of the strongest prognostic factors in melanoma. Rather than profiling via mass-gene arrays, focused analysis of gene expression using functionally relevant gene microarray can identify genes that are functionally significant. In this study, using fresh human tissue and functionally-focused cDNA microarray, we have shown that LIMK1 (cell motility regulatory gene) and VEGF (pro-angiogenic gene) are biologically relevant molecular targets with adequate predictive power to detect melanoma progression and lymph node metastasis. In addition to their potential usefulness as biomarkers for detecting SLN metastasis prior to SLN biopsy, recent advances in anti-angiogenic therapies and siRNA-mediated gene silencing techniques enable these genes to serve as potential targets for future therapies.

REFERENCES

1. Boring, C C., T. S. Squires, and T. Tong, *Cancer statistics, 1992.* CA Cancer J Clin, 1992, 42(1): p. 19-38.
2. Jemal, A., et al., *Cancer statistics,* 2004. CA Cancer J Clin, 2004, 54(1): p. 8-29.
3. Rigel, D. S., *Malignant melanoma: perspectives on incidence and its effects on awareness, diagnosis, and treatment.* CA Cancer J Clin, 1996, 46(4): p. 195-8.
4. Balch, C. M., et al., *Final version of the American Joint Committee on Cancer staging system for cutaneous melanoma.* J Clin Oncol, 2001, 19(16): p. 3635-48.
5. Belch, C. M., et al., *Prognostic factors analysis of 17,600 melanoma patients: validation of the American Joint Committee on Cancer melanoma staging system.* J Clin Oncol, 2001, 19(16): p. 3622-34.
6. Barth, A., L. A. Wanek, and D. L. Morton, *Prognostic factors in 1,521 melenoma patients with distant metastases.* J Am Coll Surg, 1995, 181(3): p. 193-201.

7. Morita, R., et al., *Comparison of genetic profiles between primary melanomas and their metastases reveals genetic alterations and clonal evolution during progression.* J Invest Dermatol, 1998, 111(6): p. 919-24.
8. Rao, U. N., M. W. Jones, and S. D. Finkelstein, *Genotypic analysis of primary and metastatic cutaneous melanoma.* Cancer Genet Cytogenet, 2003, 140(1): p. 37-44.
9. Hasegawa, S., et al., *Genome-wide analysis of gene expression in intestinal-type gastric cancers using a complementary DNA microarray representing 23,040 genes.* Cancer Res, 2002, 62(23): p. 7012-7.
10. Hippo, Y., et al., *Global gene expression analysis of gastric cancer by oligonucleotide microarrays.* Cancer Res, 2002, 62(1): p. 233-40.
11. Niki, T., et al., *Expression of vascular endothelial growth factors A, B, C, and D and their relationships to lymph node status in lung adenocarcinoma.* Clin Cancer Res, 2000, 6(6): p. 2431-9.
12. Chambers, A. F. and L. M. Matrisian, *Changing views of the role of matrix metalloproteinases in metastasis.* J Natl Cancer Inst, 1997, 89(17): p. 1260-70.
13. Repp, A. C., et al., *Human uveal melanoma cells produce macrophage migration-inhibitory factor to prevent lysis by NK cells.* J Immunol, 2000, 165(2): p. 710-5.
14. Rumpler, G., at al., *Identification of differentially expressed genes in models of melanoma progression by cDNA array analysis: SPARC, MIF and a novel cathepsin protease characterize aggressive phenotypes.* Exp Dermatol, 2003, 12(6): p. 761-71.
15. Morton, D. L., et al., *Intraoperative lymphatic mapping and selective cervical lymphadenectomy for early-stage melanomas of the head and neck.* J Clin Oncol, 1993, 11(9): p. 1751-6.
16. Morton, D. L., et al.1 *Technical details of intraoperative lymphatic mapping for early stage melanoma.* Arch Surg, 1992, 127(4): p. 392-9.
17. Essner, R., et al., *Standardized probe-directed sentinel node dissection in melanoma.* Surgery, 2000, 127(1): p. 26-31.
18. Hanley, J. A. and B. J. McNeil, *The meaning and use of the area under a receiver operating characteristic (ROC) curve.* Radiology, 1982, 143(1): p. 29-36.
19. Griner, P. F., et al., *Selection and interpretation of diagnostic tests and procedures. Principles and applications.* Ann Intern Med, 1981, 94(4 Pt 2): p. 557-92.
20. Starz, H., A. De Donno, and B. R. Balda, *The Augsburg experience: histological aspects and patient outcomes.* Ann Surg Oncol, 2001, 8(9 Suppl): p. 48S-51S.
21. Reeves, M. E., et al., *Prediction of nonsentinel lymph node status in melanoma.* Ann Surg Oncol, 2003, 10(1): p. 27-31.
22. Cochran, A. J., et al., *Prediction of metastatic melanoma in nonsentinel nodes and clinical outcome based on the primary melanoma and the sentinel node.* Mod Pathol, 2004, 17(7): p. 747-55.
23. McMasters, K. M., et al., *Lessons learned from the Sunbelt Melanoma Trial.* J Surg Oncol, 2004, 86(4): p. 212-23.
24. Reintgen, D., et al., *National trials involving lymphatic mapping for melanoma: the Multicenter Selective Lymphadenectomy Trial, the Sunbelt Melanoma Trial, and the Florida Melanoma Trial.* Semin Oncol, 2004, 31(3): p. 363-73.
25. Reintgen, D. S., et al., *The staging of malignant melanoma and the Florida Melanoma Trial.* Ann Surg Oncol, 2004, 11(3 Suppl): p. 186S-91S.
26. Kriege, M. et al., *Efficacy of MRI and mammography for breast-cancer screening in women with a familial or genetic predisposition.* N Engl J Med, 2004, 351: p. 427-37.
27. van de Vijver, M. J., et al., *A gene-expression signature as a predictor of survival in breast cancer.* N Engl J Med, 2002, 347(25): p. 1999-2009.
28. van 't Veer, L. J., et al., *Gene expression profiling predicts clinical outcome of breast cancer.* Nature, 2002, 415(6871): p. 530-6.
29. Han, H., et al., *Identification of differentially expressed genes in pancreatic cancer cells using cDNA microarray.* Cancer Res, 2002, 62(10): p. 2890-6.
30. Hegde, P., et al., *Identification of tumor markers in models of human colorectal cancer using a 19,200-element complementary DNA microarray.* Cancer Res, 2001, 61(21): p. 7792-7.
31. Xing, G. H. and J. C. Zhang, *[DNA chip analysis of gene expression patterns in poorly-differentiated human stage I lung adenocarcinoma].* Zhonghua Zhong Liu Za Zhi, 2004, 26(1): p. 36-9.
32. Wikman, H., et al., *Caveolins as tumour markers in lung cancer detected by combined use of cDNA and tissue microarrays.* J Pathol, 2004, 203(1): p. 584-93.
33. Simonetti, O., et al., *Immunohistochemical expression of vascular endothelial growth factor, matrix metalloproteinase 2, and matrix metalloproteinase 9 in cutaneous melanocytic lesions.* Cancer, 2002, 95(9): p. 1963-70.
34. Stefanou, D., et al., *Immunohistochemical expression of vascular endothelial growth factor (VEGF) and C-KIT in cutaneous melanocytic lesions.* Inst J Surg Pathol, 2004, 12(2): p. 133-8.
35. Amano, T., et al., *LIM-kinase 2 induces formation of stress fibres, focal adhesions and membrane blebs, dependent on its activation by Rho-associated kinase-catalysed phosphoiylation at threonine-505.* Biochem J, 2001, 354(Pt 1): p. 149-59.
36. Arber, S., et al., *Regulation of actin dynamics through phosphorylation of cofilin by LIM-kinase.* Nature, 1998, 393(6687): p. 805-9.
37. Ohashi, K., et al., *Rho-associated kinase ROCK activates LIM-kinase 1 by phosphorylation at threonine 508 within the activation loop.* J Biol Chem, 2000, 275(5): p. 3577-82.
38. Yang, N., et al., *Cofilin phosphorylation by LIM-kinase 1 and its role in Rac-mediated actin reorganization.* Nature, 1998, 393(6687): p. 809-12.
39. Yoshioka, K., et al., *A role for LIM-kinase in cancer invasion.* Proc Natl Acad Sci USA, 2003, 100(12): p. 7247-52.
40. Proschel, C., et al., *LImk1 is predominantly expressed in neural tissues and phosphorylates serine, threonine and tyrosine residues in vitro.* Oncogene, 1995, 11(7): p. 1271-81.
41. Lee, J. H. et al., *Factors predictive of tumor-positive nonsentinel lymph nodes after tumor-positive sentinel lymph node dissection for melanoma.* J Clin Oncol, 2004, 22: p. 3677-84.

While the foregoing has been described in considerable detail and in terms of preferred embodiments, these are not to be construed as limitations on the disclosure or claims to follow. Modifications and changes that are within the purview of those skilled in the art are intended to fall within the scope of the following claims. All literatures cited herein are incorporated by reference in their entirety.

What is claimed is:

1. A composition for the treatment of melanoma cancer, comprising a transdermal drug delivery agent and one or more therapeutic compounds that regulate the expression of LIMK1 and are selected from the group consisting of SiRNAs and antisense RNAs wherein the one or more compounds include an siRNA that targets LIMK1 mRNA at

CCGCUACUGCCCCCAAACUG,  (SEQ ID NO: 1)

CUGGCCGGCCACCUGCCACUG,  (SEQ ID NO: 2)

ACCGCUACUGCCCCCAAACU,  (SEQ ID NO: 3)

CUGGCUCCCACCUGCCCACA,  (SEQ ID NO: 4)

CCGAGACCUCAACUCCCACAA,  (SEQ ID NO: 5)

GGACCGCUACUGCCCCCAAA,  (SEQ ID NO: 6)

CCGGCGCGGCGAGAGCGGACU,  (SEQ ID NO: 7)

GAGACCUCAACUCCCACAACU,  (SEQ ID NO: 8)

CUGCCCCCCGAGCUUCUUCCC, or  (SEQ ID NO: 9)

UGGGUGCUCUGAGCAAAUCAC.  (SEQ ID NO: 10)

2. The composition of claim 1, wherein the one or more compounds are admixed with a lotion, cream, emulsion, oil, liquid, or gel, or embedded in a patch.

3. The composition of claim 2, wherein the cream is a sunscreen cream.

* * * * *